US00PP20707P2

(12) United States Plant Patent
Perkins

(10) Patent No.: US PP20,707 P2
(45) Date of Patent: Feb. 2, 2010

(54) ***SALVIA* PLANT NAMED 'MES ROS'**
(50) Latin Name: ***Salvia*×hybrid**
Varietal Denomination: Mes Ros

(75) Inventor: Ralph T. Perkins, Gilroy, CA (US)
(73) Assignee: Syngenta Crop Protection AG, Basel (CH)

( * ) Notice: Subject to any disclaimer, the term of this patent is extended or adjusted under 35 U.S.C. 154(b) by 0 days.
(21) Appl. No.: 12/313,954
(22) Filed: Nov. 26, 2008
(51) Int. Cl.
*A01H 5/00* (2006.01)
(52) U.S. Cl. ..... Plt./475
(58) Field of Classification Search ..... Plt./475
See application file for complete search history.

*Primary Examiner*—Annette H Para
(74) *Attorney, Agent, or Firm*—S. Matthew Edwards

(57) ABSTRACT

A new *Salvia* plant named 'Mes Ros,' particularly distinguished by red-purple flower color, upright, well branched, dense and bushy habit, medium green foliage and large sized flowers that are early flowering.

1 Drawing Sheet

Latin name of the genus and species of the plant claimed: *Salvia*×hybrid.

Varietal denomination: 'Mes Ros'.

BACKGROUND OF THE NEW PLANT

The present invention comprises a new *Salvia*, botanically known as *Salvia*×hybrid, and hereinafter referred to by the variety name 'Mes Ros.'

'Mes Ros' is a product of a planned breeding program. The new cultivar 'Mes Ros' has red-purple flower color, upright, well branched, dense and bushy habit, medium green foliage and large sized flowers that are early flowering.

'Mes Ros' originated from an open pollination cross in a controlled breeding program in Gilroy, Calif. USA. The female parent was an unpatented, proprietary hybrid seedling (*S. greggii*×*microphylla*) identified as '156-1' with raspberry color. '156-1' has fewer flowers, larger foliage, and a taller plant habit than 'Mes Ros.' The male parent of 'Mes Ros' was unknown.

'Mes Ros' was selected as one flowering plant within the progeny of the stated cross in September 2005 in a controlled environment in Gilroy, Calif. USA. The pollination took place in July 2004 and the seed sowing in May 2005.

The first act of asexual reproduction of 'Mes Ros' was accomplished when vegetative cuttings were taken from the initial selection in the September 2005 in a controlled environment in Gilroy, Calif. USA.

Horticultural examination of plants grown from cuttings of the plant initiated in September 2005 in Gilroy, Calif. USA, and continuing thereafter, has demonstrated that the combination of characteristics as herein disclosed for 'Mes Ros' are firmly fixed and are retained through successive generations of asexual reproduction.

'Mes Ros' has not been observed under all possible environmental conditions. The phenotype may vary significantly with variations in environment such as temperature, light intensity and day length.

A Plant Breeder's Right for this cultivar was applied for in Canada on Dec. 24, 2007. 'Mes Ros' has not been made publicly available more than one year prior to the filing of this application.

DESCRIPTION OF THE DRAWINGS

The accompanying photographic drawing shows typical flower and foliage characteristics of 'Mes Ros' with colors being as true as possible with an illustration of this type.

The photographic drawing shows two flowering potted plants of the new variety and a close-up of the flowers, growing in a one gallon pot.

This plant was grown and photographed in Gilroy, Calif. USA in April 2008. The plant was about 4 months old.

DETAILED BOTANICAL DESCRIPTION

The measurements were taken on plants growing in Gilroy, Calif. USA in April 2008. The plants were growing in gallon pots in a greenhouse trial. These plants were about 4–5 months old.

Color Chart used: Royal Horticultural Society Colour Chart (R.H.S.) 2001

BRIEF SUMMARY OF INVENTION

The following observations, measurements, and comparisons describe plants grown Gilroy, Calif. USA. The following traits have been repeatedly observed and are determined to be basic characteristics of the new variety. The combination of these characteristics distinguishes this *Salvia* as a new and distinct variety.

TABLE 1

DIFFERENCES BETWEEN THE NEW CULTIVAR 'MES ROS' AND A SIMILAR VARIETY

| | 'Mes Ros' | 'Navajo Rose' |
|---|---|---|
| Floriferousness | More flowers | Less flowers |
| Foliage size | Larger | Smaller |
| Plant habit | More compact | Less compact |

Plant:

*Form, growth and habit.*—Upright, well branching, dense and bushy.

*Plant height.*—28–31 cm.

*Plant height* (*inflorescence included*).—39–42 cm.

*Plant width.*—30–35 cm.

Foliage:
- *Type*.—Simple, opposite.
- *Immature, leaf color, upper surface*.—Closest to RHS 146B.
- *Lower surface*.—Closest to RHS 147B.
- *Mature, leaf color, upper surface*.—Closest to RHS 146A.
- *Lower surface*.—Closest to RHS 147B.
- *Length*.—4.2–5.4 cm.
- *Width*.—2.4–2.7 cm.
- *Shape*.—Ovate.
- *Base shape*.—Attenuate.
- *Apex shape*.—Obtuse to slightly acute.
- *Margin*.—Crenulate.
- *Texture, upper surface*.—Muriculate.
- *Texture, lower surface*.—Muriculate.
- *Fragrant*.—Heavily "sage" like.
- *Color of veins, upper surface*.—RHS 144A.
- *Color of veins, lower surface*.—RHS 144A.
- *Petioles color*.—RHS 144A.
- *Petioles length*.—0.7–1.4 cm.
- *Diameter of petiole*.—0.1 cm.
- *Texture*.—Hispid.

Stem:
- *Number of main branches per plant*.—3–4.
- *Number of leaves per stem*.—12–16.
- *Color of stem*.—RHS 146C.
- *Length of stem*.—25–30 cm.
- *Diameter*.—0.3 cm.
- *Length of internodes*.—2–3 cm.
- *Texture*.—Hispid.

Inflorescence:
- *Type*.—Terminal raceme.
- *Blooming habit*.—Flowers continuously from spring through the fall.
- *Number of racemes per plant*.—35–40.
- *Duration of flowering*.—Continuous flowering throughout the summer.
- *Color of peduncle*.—RHS 146C.
- *Length of peduncle*.—8–16 cm.
- *Peduncle diameter*.—0.1–0.15 cm.
- *Texture*.—Hispid; glandular hairs.
- *Color of pedicel*.—RHS 146D.
- *Length of pedicel*.—0.3–0.4 cm.
- *Diameter of pedicel*.—0.1 cm.
- *Texture*.—Hispid.

Corolla:
- *Form*.—Single, bilabiate; with one upper lip, with one lower lip with three lobes consisting one a mid-lobe and 2 small lateral lobes; fused at base; upper lip wraps around the pistil.
- *Lastingness of individual bloom on the plant*.—5–6 days.
- *Fragrance*.—"Sage" like.
- *Immature florets general color, upper surface*.—Closest to RHS N57A but deeper.
- *Lower surface*.—RHS 67A.
- *Mature florets vertical height of floret*.—1.8–2.0 cm.
- *Horizontal width of floret*.—1.8–2.0 cm.
- *Depth of floret*.—2.4–2.5 cm.
- *Color upper lip, upper surface*.—Closest to RHS N57B but appears brighter because of the RHS N66A color of the villous hairs.
- *Color upper lip, lower surface*.—RHS 67A.
- *Length of upper lip*.—0.8–0.9 cm.
- *Width of upper lip*.—0.3–0.4 cm.
- *Shape*.—Obovate.
- *Apex shape*.—Obtuse.
- *Margin*.—Entire.
- *Texture, outer surface*.—Papillose; villous hairs of RHS 66A at the apex.
- *Inner surface*.—Glabrous.
- *Color lower lip, mid-lobe, upper surface*.—RHS N57A.
- *Color lower lip, mid-lobe, lower surface*.—RHS 67A.
- *Length of lower lip, mid-lobe*.—1.3–1.4 cm.
- *Width of lower lip, mid-lobe*.—1.2–1.3 cm.
- *Shape*.—Obcordate.
- *Apex shape*.—Emarginate.
- *Margin*.—Appears very slightly laciniate.
- *Texture, upper surface*.—Papillose.
- *Lower surface*.—Glabrous and slightly hispid.
- *Color lower lip, lateral lobe, upper surface*.—RHS N57B.
- *Color lower lip, lateral lobe, lower surface*.—RHS 67A.
- *Length of lower lip, lateral lobe*.—0.6 cm.
- *Width of lower lip, lateral lobe*.—0.3 cm.
- *Petal shape*.—Oblong.
- *Apex shape*.—Obtuse.
- *Margin*.—Entire.
- *Texture, upper surface*.—Papillose.
- *Lower surface*.—Glabrous.
- *Corolla, color, outer surface*.—RHS 67A.
- *Inner surface*.—RHS 55B but RHS N155B stripes.
- *Length of corolla*.—1.5 cm.
- *Width of corolla*.—0.7 cm at the widest.
- *Texture, outer upper surface*.—Slightly hispid.
- *Texture, outer lower surface*.—Glabrous.
- *Texture, inner surfaces*.—Glabrous.

Bud (just before opening):
- *Color*.—RHS 71A.
- *Length*.—1.0–1.2 cm.
- *Width*.—0.3–0.4 cm.
- *Shape*.—Tubular to oblong.

Calyx:
- *Number of sepals*.—2, fused into a tube form.
- *Color of sepals, upper surface, upper most sepal*.—RHS 144C ground color; RHS 176A stripes of anthocyanins.
- *Lower most sepals*.—RHS 144C ground color; RHS 176A at the apex.
- *Inner surface of all sepals*.—RHS 147C.
- *Length of sepals*.—1.0–1.1 cm.
- *Width of sepals*.—0.2–0.4 cm.
- *Sepal shape*.—Broadly linear.
- *Apex shape*.—Acute.
- *Margin*.—Entire.
- *Texture, outer surface*.—Hispid.
- *Inner surface*.—Glabrous.

Reproductive organs:
- *Pistil*.—1.
- *Length*.—2.5 cm.
- *Style color*.—RHS N155B but whiter.
- *Style length*.—2.1–2.3 cm.
- *Stigma color*.—RHS 77D.
- *Stamens*.—2.
- *Color of filaments*.—RHS N155B but whiter.
- *Length of filaments*.—1.1 cm.
- *Anther color*.—RHS 15A.
- *Anther length*.—0.15–0.2 cm.

*Color of pollen*.—RHS 17B.

*Pollen amount*.—Moderate.

*Fertility/seed set*.—Not observed on this hybrid.

Disease/pest resistance: Disease resistance or susceptibility has not been observed on this hybrid.

What is claimed is:

1. A new and distinct variety of *Salvia* plant named 'Mes Ros,' substantially as illustrated and described herein.

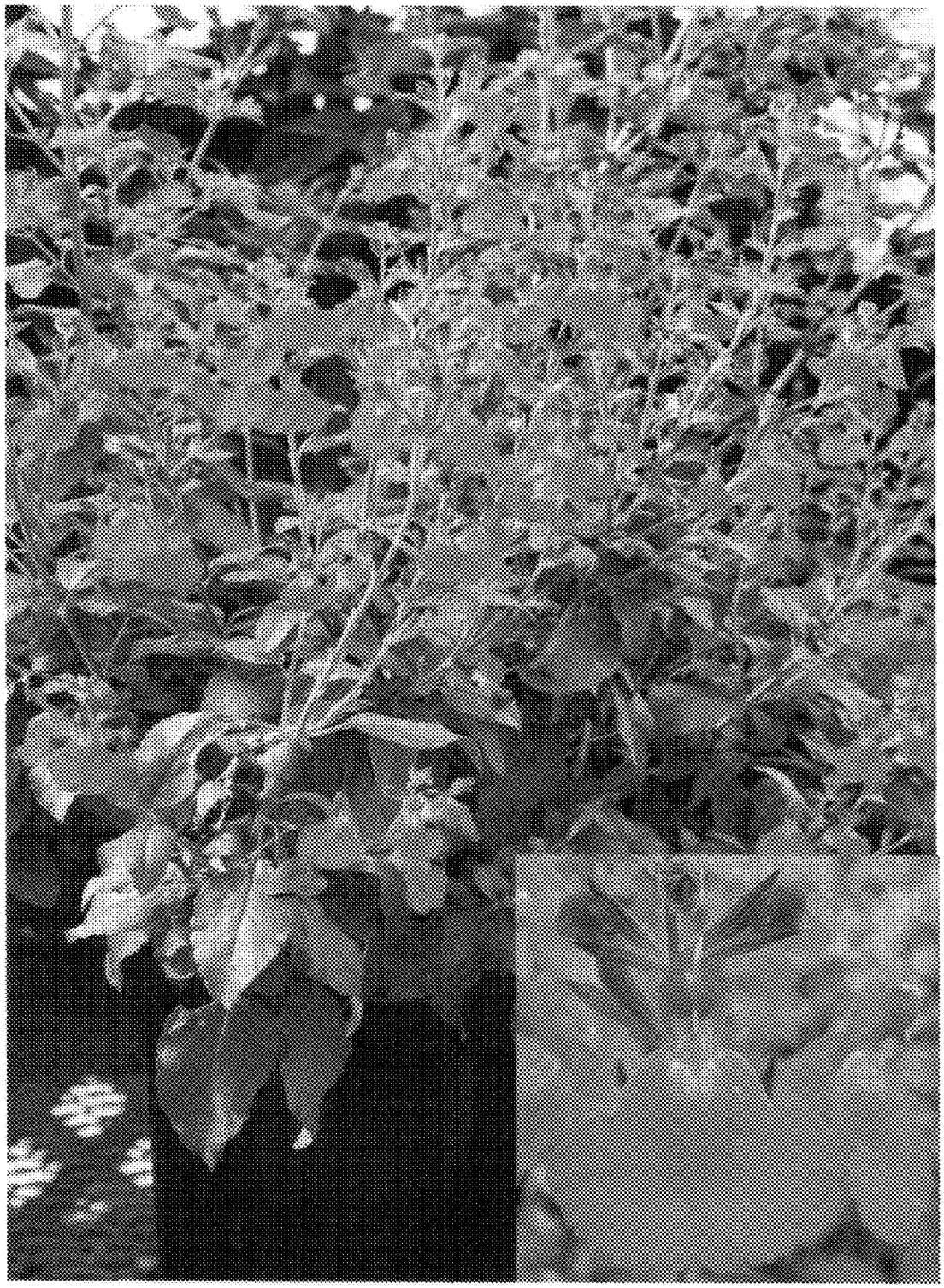

* * * * *